United States Patent
Uckun et al.

(10) Patent No.: US 6,825,177 B2
(45) Date of Patent: Nov. 30, 2004

(54) ARYL PHOSPHATE DERIVATIVES OF D4T WITH POTENT ANTI-VIRAL ACTIVITY

(75) Inventors: Fatih Uckun, White Bear Lake, MN (US); Chun-Lin Chen, Roseville, MN (US); Taracad K. Venkatachalam, Maplewood, MN (US); Zhoa-Hai Zhu, Shoreview, MN (US)

(73) Assignee: Parker Hughes Institute, St. Paul, MN (US)

( * ) Notice: Subject to any disclaimer, the term of this patent is extended or adjusted under 35 U.S.C. 154(b) by 36 days.

(21) Appl. No.: 10/037,003

(22) Filed: Oct. 19, 2001

(65) Prior Publication Data

US 2002/0137726 A1 Sep. 26, 2002

Related U.S. Application Data

(60) Provisional application No. 60/299,885, filed on Jun. 21, 2001, and provisional application No. 60/244,263, filed on Oct. 30, 2000.

(51) Int. Cl.$^7$ .................. A61K 31/70; A61K 31/66; A61K 31/40
(52) U.S. Cl. .................. 514/51; 514/132; 514/414
(58) Field of Search .................. 514/51, 132, 414

(56) References Cited

PUBLICATIONS

Mcuigan et al, 128CA:289775 , 1998.*
Periguad et al, 126CA:271667 1996.*
Valquest, BO, 30CA:856, 1935.*
Keller, R, 62CA:6881e–h, 1963.*

* cited by examiner

Primary Examiner—Russell Travers
(74) Attorney, Agent, or Firm—Merchant & Gould P.C.

(57) ABSTRACT

Methods for increasing the elimination half-life of key metabolites such as d4T by administering an aryl phosphate derivative of d4T having an electron withdrawing substituent on the aryl group and an amino acid substituent on the phosphate group are described. A preferred aryl phosphate derivative of d4T is HI-113 (d4T-5'-[p-bromophenyl methoxyalaninyl phosphate]). The administration of HI-113 results in more prolonged systemic exposure to the key metabolites, Ala-d4T-MP and d4T, than administration of an equimolar dose of either metabolite. Each metabolite has a significantly longer elimination half life when formed in vivo from the administration of HI-113 than when the metabolite is administered directly.

39 Claims, 10 Drawing Sheets

ARYL PHOSPHATE DERIVATIVES OF D4T WITH POTENT ANTI-VIRAL ACTIVITY

This application claims priority from provisional application Ser. No. 60/299,885, filed Jun. 21, 2001 and provisional application Ser. No. 60/244,263, filed Oct. 30, 2000, both of which are incorporated herein by reference.

FIELD OF THE INVENTION

The invention is directed to methods of treating viral infections through the administration of aryl phosphate derivatives of 2',3'-didehydro-2',3'-dideoxythymidine.

BACKGROUND OF THE INVENTION

One approach to treating AIDS is by inhibiting the reverse transcriptase (RT) activity of the human immune deficiency virus (HIV). Potent inhibitors of HIV RT are known and include 5'-triphosphates of 2',3'-dideoxynucleoside (hereinafter "ddN") analogues such as 3'-azido-3'-deoxythymidine (hereinafter "AZT") and 2',3'-didehydro-2',3'-dideoxythymidine (hereinafter "d4T"). These active RT inhibitors are generated intracellularly by the action of nucleoside kinase and nucleotide kinase.

The rate-limiting step for the conversion of AZT to its bioactive metabolite AZT-triphosphate seems to be the conversion of the monophosphate derivative to the diphosphate derivative, whereas the rate-limiting step for the intracellular generation of the bioactive d4T metabolite d4T-triphosphate was reported to be the conversion of the nucleoside to its monophosphate derivative. (Balzarini et al., 1989, *J.Biol. Chem.* 264:6127; McGuigan et al., 1996, *J. Med. Chem.* 39:1748).

In an attempt to overcome the dependence of ddN analogues on intracellular nucleoside kinase activation, McGuigan et al. prepared aryl methoxyalaninyl phosphate derivatives of AZT (McGuigan et al., *J.Med. Chem.*, 36, 1048 (1993); McGuigan et al., *Antiviral Res.* 17, 311(1992)) and d4T (McGuigan et al., *J.Med. Chem.*, 39, 1748 (1996); McGuigan et al., *Bioorg. Med.Chem.Lett.*, 6, 1183 (1996)). Such compounds undergo intracellular hydrolysis to yield monophosphate derivatives that are further phosphorylated by thymidylate kinase to give the bioactive triphosphate derivatives in a thymidine kinase (TK)-independent fashion.

U.S. Pat. No. 6,030,957 (Uckun et al.) disclosed that substitution of the aryl moiety of an aryl phosphate derivative of d4T enhances the ability of the compounds to undergo hydrolysis. Such compounds are potent antiviral agents. A particularly potent compound is HI-113, (d4T-5'-[p-bromophenyl methoxyalaninyl phosphate]).

SUMMARY OF THE INVENTION

The invention is directed to aryl phosphate derivatives of 2',3'-didehydro-2',3'-dideoxythymidine (hereinafter "d4T") that inhibit human immune deficiency virus reverse transcriptase (HIV RT) and exhibit potent anti-viral activity. One aspect of the invention provides methods for treating viral infections by increasing the elimination half-life of key metabolites such as d4T in a mammal. The method comprises administering an aryl phosphate derivative of d4T having an electron withdrawing substituent on the aryl group and an amino acid substituent on the phosphate group as in Formula I:

Formula I where $R_1$ is an aryl group substituted with an electron withdrawing group and $R_2$ is an amino acid or an ester of an amino acid. In one embodiment of Formula I, $R_1$ is a phenyl substituted with an electron withdrawing group and $R_2$ is an ester of an α-amino acid. Preferably, Formula I is HI-113 (d4T-5'-[p-bromophenyl methoxyalaninyl phosphate]) where $R_1$ is phenyl group substituted with bromo at the para position and $R_2$ is the methyl ester of alanine.

The oral or intravenous administration of HI-113 results in the formation of two key metabolites: alaninyl-d4T-monophosphate (Ala-d4T-MP) and d4T. The administration of HI-113 results in more prolonged systemic exposure to Ala-d4T-MP as well as d4T than administration of an equimolar dose of either metabolite. Each metabolite has a significantly longer elimination half life when formed from the administration of HI-113 than when administered directly.

Another aspect of the invention provides a method for treating viral infections comprising extending the elimination half-life of d4T in a mammal by administering an effective amount of a compound of Formula IV:

Formula IV where $R_2$ is an amino acid or amino acid ester residue. In one embodiment, $R_2$ is the methyl ester of alanine.

The methods of the invention can be used to treat HIV.

DETAILED DESCRIPTION OF THE INVENTION

The invention is directed to aryl phosphate derivatives of 2',3'-didehydro-2',3'-dideoxythymidine (hereinafter "d4T") that inhibit human immune deficiency virus reverse transcriptase (HIV RT) and exhibit potent anti-viral activity. More particularly, the present invention provides methods for increasing the elimination half-life of key metabolites such as d4T in a mammal by administering an aryl phosphate derivative of d4T having an electron withdrawing substituent on the aryl group and an amino acid substituent on the phosphate group as in Formula I:

Formula I where $R_1$ is an aryl group substituted with an electron withdrawing group and $R_2$ is an amino acid or an ester of an amino acid. The term "aryl" includes aromatic groups such as, for example, phenyl, naphthyl, and anthryl. Suitable electron-withdrawing groups include halo (—Br, —Cl, —I, —F), —$NO_2$, —CN, —$SO_3H$, —COOH, —CHO, —COR (where R is a ($C_1$ to $C_4$) alkyl), and the like.

The term "amino acid" refers to any of the naturally occurring amino acids, as well as their opposite enantiomers or racemic mixture of both enantiomers, synthetic analogs, and derivatives thereof. The term includes, for example, α-, β-, γ-, δ-, and ω-amino acids. Suitable naturally occurring amino acids include glycine, alanine, valine, leucine, isoleucine, proline, threonine, serine, methionine, cysteine, aspartic acid, asparagine, glutamic acid, glutamine, arginine, lysine, phenylalanine, tryptophan, tyrosine, and histidine. Synthetic, or unnatural, amino acids such as, for example, trifluoroleucine, p-fluorophenylalanine, and 3-triethylalanine can be used. The term amino acid includes esters of the amino acids. Esters include lower alkyl esters in which the alkyl group has one to seven carbon atoms, preferably one to four carbon atom such as, for example, methyl, ethyl, propyl, and butyl. The amino group of the amino acid or ester thereof is attached to the phosphate group in Formula I.

The compounds of Formula I can also be in the form of pharmaceutically acceptable salts. Pharmaceutically acceptable salts are formed with organic and inorganic acids. Examples of suitable acids for salt formation with the amino group of the amino acid or amino acid ester residue are hydrochloric, sulfuric, phosphoric, acetic, citric, oxalic, malonic, salicylic, malic, gluconic, fumaric, succinic, asorbic, maleic, methanesulfonic, and the like. The salts are prepared by contacting the free base form with a sufficient amount of the desired acid to produce either a mono or di, etc. salt in the conventional manner. Suitable bases for the formation of a salt with the carboxylate group of the amino acid residue include, for example, sodium hydroxide, sodium carbonate, sodium bicarbonate, potassium hydroxide, potassium carbonate, and potassium bicarbonate.

In one embodiment of Formula I, $R_1$ is a phenyl group substituted with an electron withdrawing group and $R_2$ is an α-amino acid or ester thereof as shown in Formula II:

Formula II

In Formula II, X is an electron-withdrawing group such as halo (—Br, —Cl, —I, —F), —$NO_2$, —CN, —$SO_3H$, —COOH, —CHO, —COR (where R is a ($C_1$ to $C_4$) alkyl), and the like. $R_3$ is hydrogen or an alkyl of one to seven carbon atoms. preferably of one to four carbon atoms such as, for example, methyl, ethyl, propyl, and butyl. $R_4$ is hydrogen (e.g., as in glycine), an alkyl (e.g. as in alanine, valine, leucine, isoleucine, proline), a substituted alkyl (e.g., as in threonine, serine, methionine, cysteine, aspartic acid, asparagine, glutamic acid, glutamine, arginie, and lysine), an arylalkyl (e.g., as in phenylalanine and tryptophan), a substituted arylalkyl (e.g., as in tyrosine), or a heteroalkyl (e.g., as in histidine).

One embodiment of Formula II is HI-113 (d4T-5'-[p-bromophenyl methoxyalaninyl phosphate]) where X is bromo attached to the phenyl group in the para position, $R_4$ is methyl, and $R_3$ is methyl. HI-113 is shown in Formula III:

Formula III

Previous in vitro studies showed that an electron withdrawing group at the para position of the phenyl group enhances the rate of hydrolysis and thereby enhances production of a key metabolite alaninyl-d4T-monophosphate (Ala-d4T-MP) relative to the unsubstituted aryl phosphate derivative (Venkatachalam et al., *Bioorg. Med. Chem. Lett.*, 8, 3121 (1998); Vig et al., *Antiviral Chem. Chemother.*, 9, 445 (1998); and U.S. Pat. No. 6,030,957 (Uckun et al.)). HI-113 is substantially more potent than d4T in inhibiting HIV replication in human peripheral blood mononuclear cells (PBMNC) or thymidine kinase-deficient T-cells. HI-113 inhibits the replication of HIV-2 and zidovudine (ZVD/AZT)-resistant HIV-1 strains in PBMNC at nanomolar concentrations.

The present invention resulted from in vivo studies using various d4T derivatives. The anti-viral agent HI-113 is quickly metabolized in vivo to form two metabolites: 2',3'-didehydro-3'-deoxythymidine (d4T) and alaninyl-d4T-monophosphate (Ala-d4T-MP) as shown in Scheme 1. Ala-d4T-MP can also be metabolized further to yield d4T. The metabolite d4T had not been found in the earlier in vitro studies with cells.

Scheme 1

Figure 2:
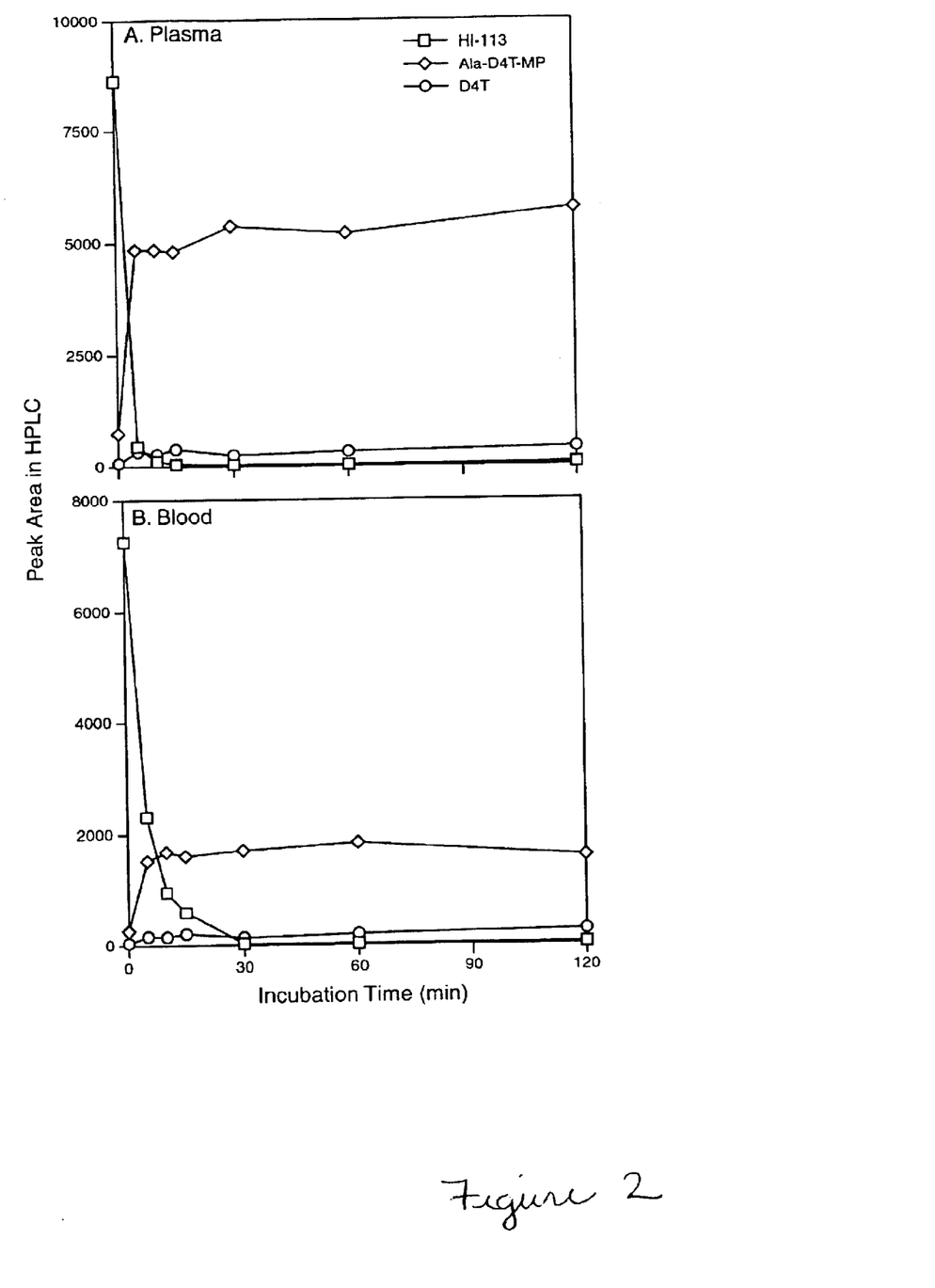
FIG. 2 is a plot showing the stability of HI-113 in plasma (A) and in whole blood (B) as a function of time.

HI-113 readily metabolizes in either plasma or whole blood to form Ala-d4T-MP (see FIG. 2). Only a small amount of d4T forms. Ala-d4T-MP is stable both in plasma and in whole blood. These results indicate that other enzymes (e.g., liver enzymes) are needed for formation of d4T by hydrolysis of either Ala-d4T-MP or HI-113. This hypothesis is consistent with the formation of a significant amount of d4T after incubation of HI-113 with a liver homogenate (see FIG. 4).

Figure 3:
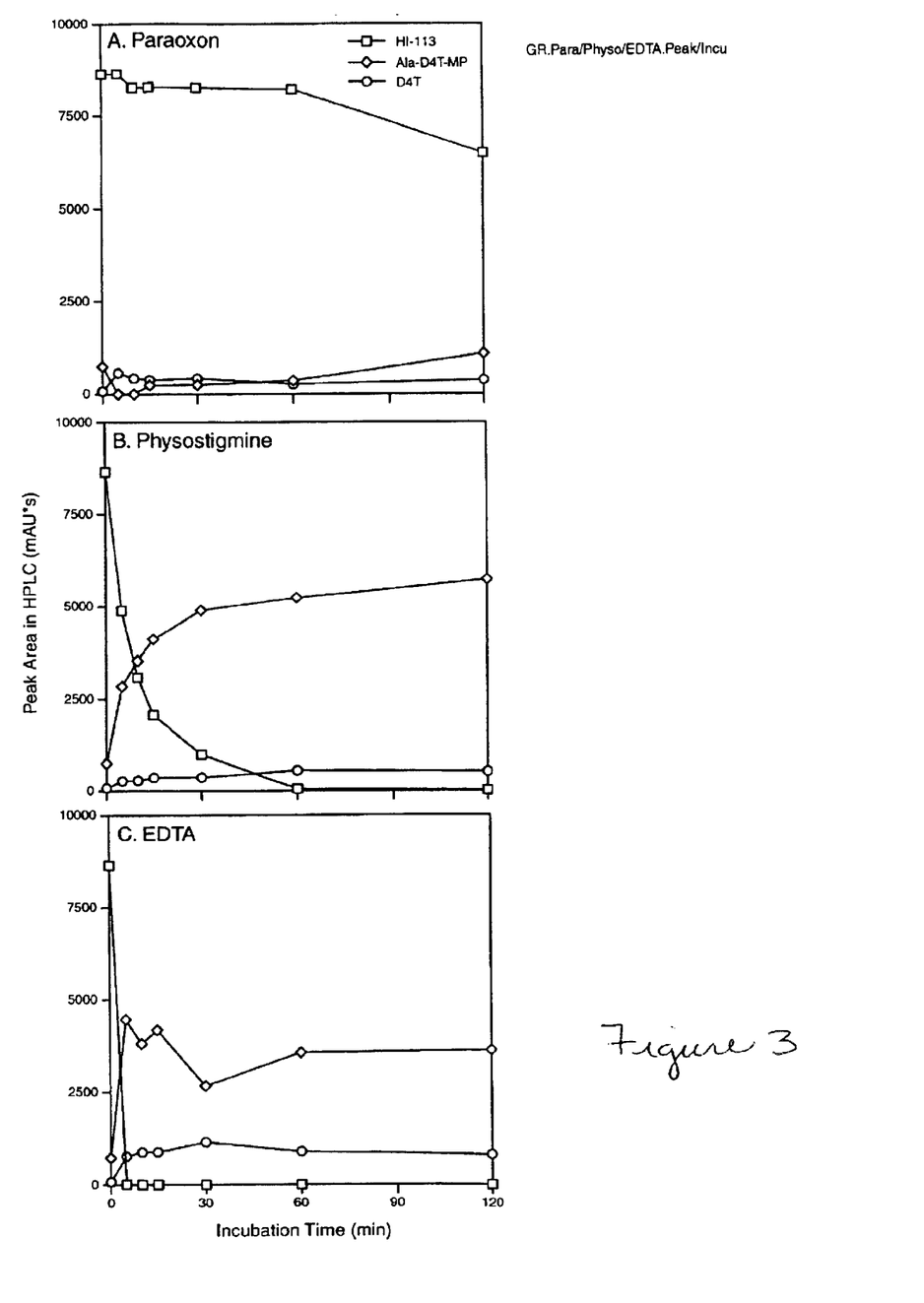
FIG. 3 is a plot showing the stability of HI-113 and the formation of key metabolites in plasma in presence of paraozon (A), physostigmine (B), and EDTA (C) as a function of time.

Paraoxon, an inhibitor of both cholinesterase and carboxylesterase (Augustinsson, *Ann. N. Y Acad. Sci.*, 94, 884 (1961); McCracken et al., *Biochem. Pharmacol.*, 46, 1125 (1993); Madhu et al., *J. Pharm. Sci.*, 86, 971 (1997)), significantly prevented the hydrolysis of HI-113 to Ala-d4T-MP and d4T, suggesting that both cholinesterase and carboxylesterase are important for metabolism of HI-113 (see FIG. 3A). Physostigmine, an inhibitor of cholinesterase, partially prevented the hydrolysis of HI-113, which further supports the importance of cholinesterase in hydrolysis of HI-113 (see FIG. 3B). EDTA, an inhibitor of arylesterase, did not affect the hydrolysis of HI-113, indicating that arylesterase is probably not involved in the hydrolysis of HI-113 (see FIG. 3C).

The elimination half-life of intravenously administered d4T was fairly similar to the elimination half-life of d4T formed after intravenous administration of Ala-d4T-MP ($t_{1/2}$ of 30.3 minutes vs. 34.0 minutes). In contrast, the elimination half-life for d4T formed after intravenous administration of HI-113 was significantly prolonged ($t_{1/2}$ of 114.8 minutes). Similarly, the elimination half-life for Ala-d4T-MP formed from HI-113 was significantly longer than the $t_{1/2}$ for Ala-d4T-MP administered intravenously ($t_{1/2}$ of 129.2 minutes vs. 28.5 minutes). The intravenous administration of HI-113 results in prolonged systemic exposure to both Ala-d4T-MP and d4T compared to administration of equimolar dose of Ala-d4T-MP or d4T due to apparently longer elimination half-lives of HI-113-derived metabolites.

Following intravenous administration, the elimination half-life ($t_{1/2}$) of HI-113 was 3.5 minutes with a systemic clearance (CL) of 160.9 ml/min/kg. Different estimates for systemic clearance (CL) values were obtained for the two diastereomers of HI-113 (HI-113A is 208.2 ml/min/kg and HI-113B is 123.9 ml/min/kg), but both were completely metabolized within 30 minutes. HI-113 was converted to the active metabolites Ala-d4T-MP (23%) and d4T (24%). The $t_{max}$ values for Ala-d4T-MP and d4T formed from intravenously administered HI-113 were 5.9 minutes and 18.7 minutes, respectively.

Intravenous administration of Ala-d4T-MP results in formation of d4T (15%). Ala-d4T-MP can also be used as a d4T prodrug. The invention provides a method for treating viral infections comprising extending the elimination half-life of d4T in a mammal by administering an effective amount of a compound of Formula IV:

Formula IV where $R_2$ is an amino acid or esterified thereof.

The compounds of Formula IV can also be in the form of pharmaceutically acceptable salts. Pharmaceutically acceptable salts are formed with organic and inorganic acids. Examples of suitable acids for salt formation with the amino group of the amino acid or amino acid ester residue are hydrochloric, sulfuric, phosphoric, acetic, citric, oxalic, malonic, salicylic, malic, gluconic, fumaric, succinic, asorbic, maleic, methanesulfonic, and the like. The salts are prepared by contacting the free base form with a sufficient amount of the desired acid to produce either a mono or di, etc. salt in the conventional manner. Suitable bases for the formation of a salt with the carboxylate group of the amino acid residue include, for example, sodium hydroxide, sodium carbonate, sodium bicarbonate, potassium hydroxide, potassium carbonate, and potassium bicarbonate.

Orally administered HI-113 also yielded Ala-d4T-MP and d4T as the major metabolites. No parent HI-113 was detectable in the blood after oral administration. Although HI-113 is stable in gastric fluid and can be absorbed in the stomach, it can quickly hydrolyze in blood. On the other hand, HI-113 decomposes readily in intestinal fluid to form Ala-d4T-MP.

This metabolite can be absorbed in the intestine and then further metabolized to yield d4T in the blood. The $t_{max}$ and $t_{1/2}$ values for d4T in mice were longer when derived from orally administered HI-113 (42.4 minutes and 99.0 minutes, respectively) than from orally administered d4T (5 minutes and 18 minutes, respectively). The $t_{max}$ value is higher but the $t_{1/2}$ value is lower for orally administered HI-113 compared to intravenously administered HI-113. The estimated bioavailabilities of Ala-d4T-MP and d4T were approximately 12% and 48%, respectively, after oral administration of HI-113. However, the bioavailability of d4T metabolized from HI-113 (48%) was lower than that of orally administered D4T (98%).

The methods of the invention can be used, for example, to treat HIV.

Administration Methods

Compounds of Formulas I to IV can be formulated as pharmaceutical compositions and administered to a mammalian host, including a human patient in a variety of forms adapted to the chosen route of administration. The compounds are typically administered in combination with a pharmaceutically acceptable carrier, and can be combined with specific delivery agents, including targeting antibodies or cytokines.

The compounds can be administered orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions, or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

EXAMPLES

The synthetic procedures for the preparation of HI-113, Ala-d4T-MP and d4T have been previously described in detail (Venkatachalam et al., *Bioorg. Med. Chem. Lett.*, 8, 3121 (1998); Vig et al., *Antiviral Chem. Chemother.*, 9, 445, (1998); U.S. Pat. No. 6,030,957 (Uckun et al.)) and are incorporated herein by reference.

Example 1

Quantitative HPLC for Detection of HI-113 and its Metabolites

The HPLC system used for these studies was a Hewlett Packard (Palo Alto, Calif.) series 1100 instrument equipped with a quaternary pump, an autosampler, an automatic electronic degasser, an automatic thermostatic column compartment, a diode array detector and a computer with Chemstation software for data analysis (Chen et al., *J. Chromatogr. B.*, 724, 157 (1999); Chen et al., *J. Chromatogr. B.*, 727, 205 (1999); and Chen et al., *J. Liq. Chromatogr.*, 22, 1771 (1999)). The analytical column used was a Zobax SB-Phenyl (5 µm, Hewlett Packard, Inc.) column attached to a guard column (Hewlett Packard, Inc.). The column was equilibrated prior to data collection. The linear gradient mobile phase (flow rate=1.0 mL/min) was: 100% A/0% B at 0 minutes, 88% A/12% B at 20 minutes, 8% A/92% B at 30 minutes (A: 10 mM ammonium phosphate buffer, pH 3.7; B: acetonitrile). The detection wavelength was 268 nm, the peakwidth was less than 0.03 minutes, the response time was 0.5 seconds, and the slit was 4 nm.

HPLC-grade reagents and deionized, distilled water were used in this study. Acetonitrile was purchased from Burdick & Jackson (Allied Signal Inc., Muskegon, Mich.). Acetic acid was purchased from Fisher Chemicals (Fair Lawn, N.J.). Ammonium phosphate and phosphoric acid were purchased from Sigma-Aldrich (St. Louis, Mo.).

Plasma samples (200 µL) were mixed 1:4 with acetone (800 µL) and vortexed for at least 30 seconds. Following centrifugation, the supernatant was transferred into a clean tube and was dried under nitrogen. A 50 µL solution of 50% methanol in 200 mM HCl was used to reconstitute the extraction residue, and 40 µL was injected into the HPLC.

Figure 1:
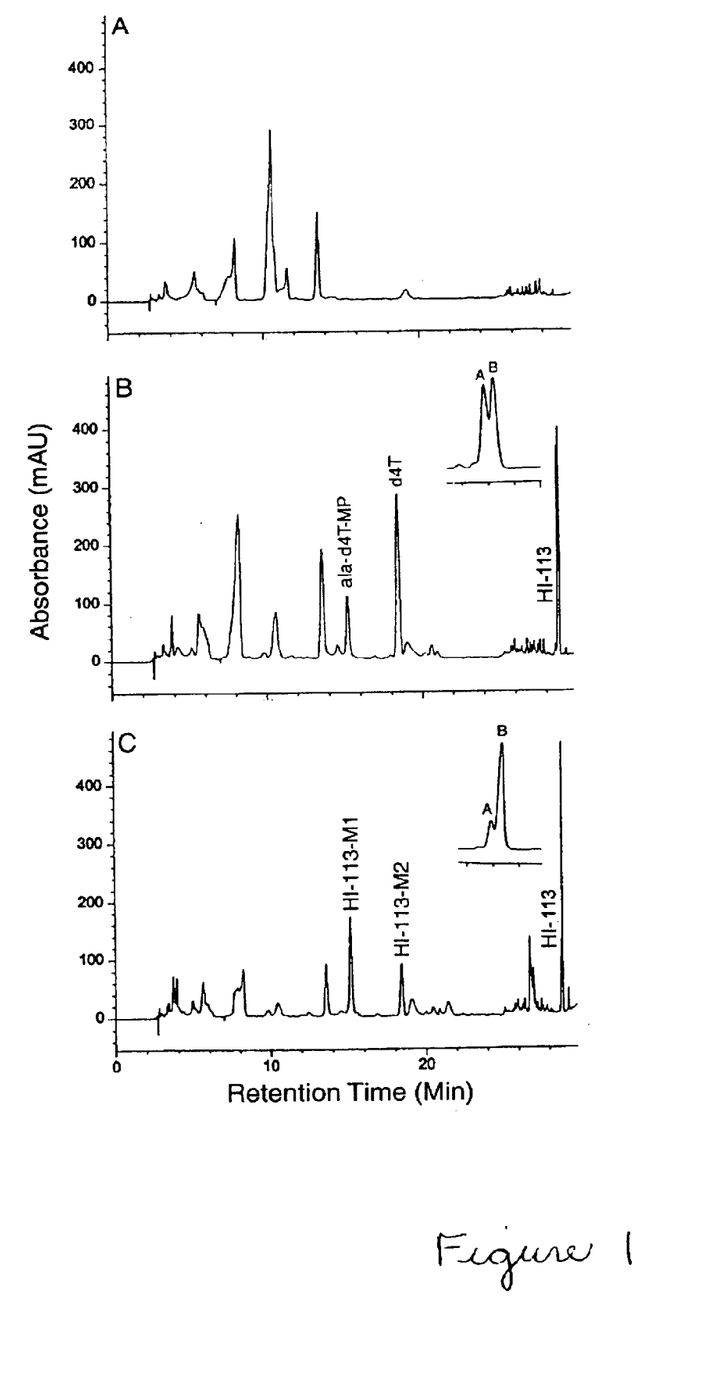
FIG. 1 shows representative HPLC chromatograms of blank plasma (A), blank plasma spiked with HI-113, d4T and Ala-d4T-MP (B), and plasma samples 10 minutes after intravenous injection of 100 mg/kg HI-113 (C).

The chromatographic retention times (RT) measured for HI-113 and its metabolites in spiked samples were 28.7±0.02 minutes (HI-113A; n=13; FIG. 1B), 28.9±0.02 minutes (HI-113B; n=13; FIG. 1C), 15.3±0.2 minutes (Ala-d4T-MP; n=30) and 18.5±0.1 minutes (d4T; n=30). HI-113A and HI-113B are diastereomers of HI-113. At these retention times, no significant interference peaks from the blank plasma were observed (FIGS. 1A and 1B).

The hydrochloric acid component of the reconstituted solutions played a key role in the chromatography of HI-113 and its metabolites. The acid protonated Ala-d4T-MP and no peak appeared in the chromatogram for this metabolite if there was no hydrocholoric acid in the reconstituted solution. The acidic solution decreased the stability of Ala-d4T-MP, however. Therefore, all of the extracted samples were analyzed immediately after reconstitution.

Example 2

Stability of HI-113 and Ala-d4T-MP in Whole Blood and Plasma

Whole blood and plasma samples were spiked with HI-113 and Ala-d4T-MP to yield final concentrations of 250 µM HI-113 and 100 µM Ala-d4T-MP, respectively. The whole blood samples were placed in a 37° C. water bath, while plasma samples were stored at −20° C. At a predetermined time, an aliquot (100 µl) of spiked whole blood or plasma was extracted by adding 400 µl of acetone to induce precipitation of proteins, as described above. The absolute peak area was used to evaluate the stability of HI-113 and Ala-d4T-MP.

The results shown in FIGS. 2A and 2B indicate that HI-113 is very unstable in plasma and in whole blood. Following incubation with plasma, over 95% of the HI-113 decomposed after 5 minutes. In the whole blood samples, 68%, 87% and 92% of the HI-113 decomposed in samples taken at 5, 10 and 15 minutes, respectively. In both the plasma and whole blood samples, decomposition of HI-113 was complete within 30 minutes. (see Table 1 for plasma data). Thus, extraction of the samples was required immediately after the samples were obtained. In contrast, Ala-d4T-MP was stable in both whole blood and plasma for 1 day.

Example 3

Stability of HI-113 in Plasma in the Presence of Selective Esterase Inhibitors

Plasma samples were pre-incubated with the esterase inhibitors paraoxon (final concentration of 0.1 mM), physostigmine (final concentration of 0.1 mM), and EDTA (final concentration of 1M) at 37° C. for 30 minutes. Then HI-113 was added to yield final concentrations of 250 µM. At a predetermined time, an aliquot (100 µl) of spiked plasma was extracted by adding 400 µl of acetone to induce precipitation of proteins, as described above. Decomposition of HI-113 in plasma was significantly inhibited by paraoxon, partially inhibited by physostigmine, but not affected by EDTA (see FIGS. 3A, 3B, and 3C as well as Table 1). The data in Table 1 was the mean percent hydrolysis from two experiments.

TABLE 1

Effect of Selective Esterase Inhibitors on Metabolism of HI-113 in Plasma

| Specificity | No inhibitor | Paraoxon (0.1 mM) cholinesterase & carboxyl-esterase | Physostigmine (0.1 mM) cholinesterase | EDTA (1 mM) arylesterase |
|---|---|---|---|---|
| 5 min | 95% | 0% | 43% | 99% |
| 10 min | 98% | 2% | 65% | 100% |
| 15 min | 99% | 2% | 76% | 100% |
| 30 min | 100% | 2% | 89% | 100% |
| 60 min | 100% | 3% | 100% | 100% |
| 120 min | 100% | 24% | 100% | 100% |

Example 4

Stability of HI-113 in Murine Liver Homogenates

Fresh mouse liver was obtained from Balb/c mice and homogenated in 1×PBS (1:1, W/V) using a Polytron (PT-MR2000) homogenizer (Kinematical AG, Littau, Switzerland). HI-113 was added to the liver homogenate to yield a final concentration of 100 µM. At a predetermined time, an aliquot (100 µl) of spiked liver homogenate was extracted by adding 400 µl of acetone to induce precipitation of proteins, as described above.

Figure 4:
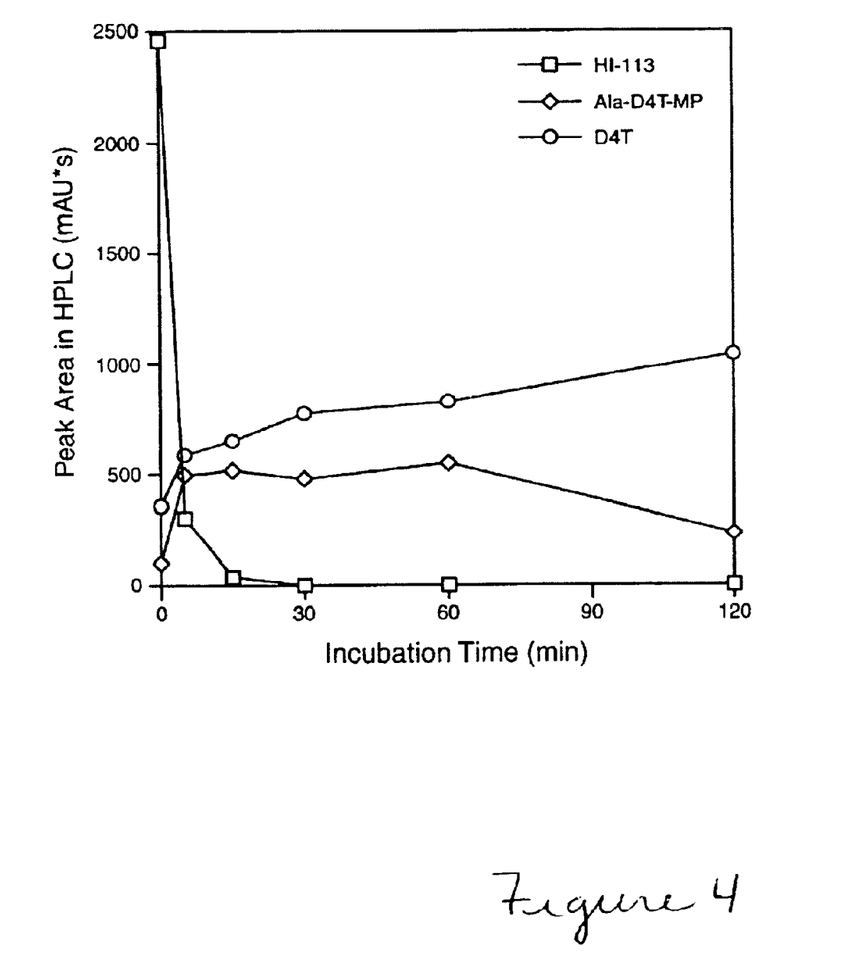
FIG. 4 is a plot showing the stability of HI-113 and the formation of key metabolites in liver homogenate as a function of time.

Like in plasma, HI-113 decomposed after incubation with the liver homogenate within 30 minutes (FIG. 4). However, unlike in plasma, significant amounts of d4T were detected after incubation with the liver homogenate.

Example 5

Stability of HI-113 and Ala-d4T-MP in Gastric and Intestinal Fluids

The simulated gastric and intestinal fluids were prepared following USP XXII and were spiked with HI-113 and Ala-d4T-MP to yield a solution with a final concentration of 100 µM of each compound. The spiked fluids were then placed in a 37° C. water bath. At a predetermined time, 100 µl aliquots of the spiked gastric or intestinal fluid were extracted by adding 400 µl of acetone as discussed above.

Figure 5:
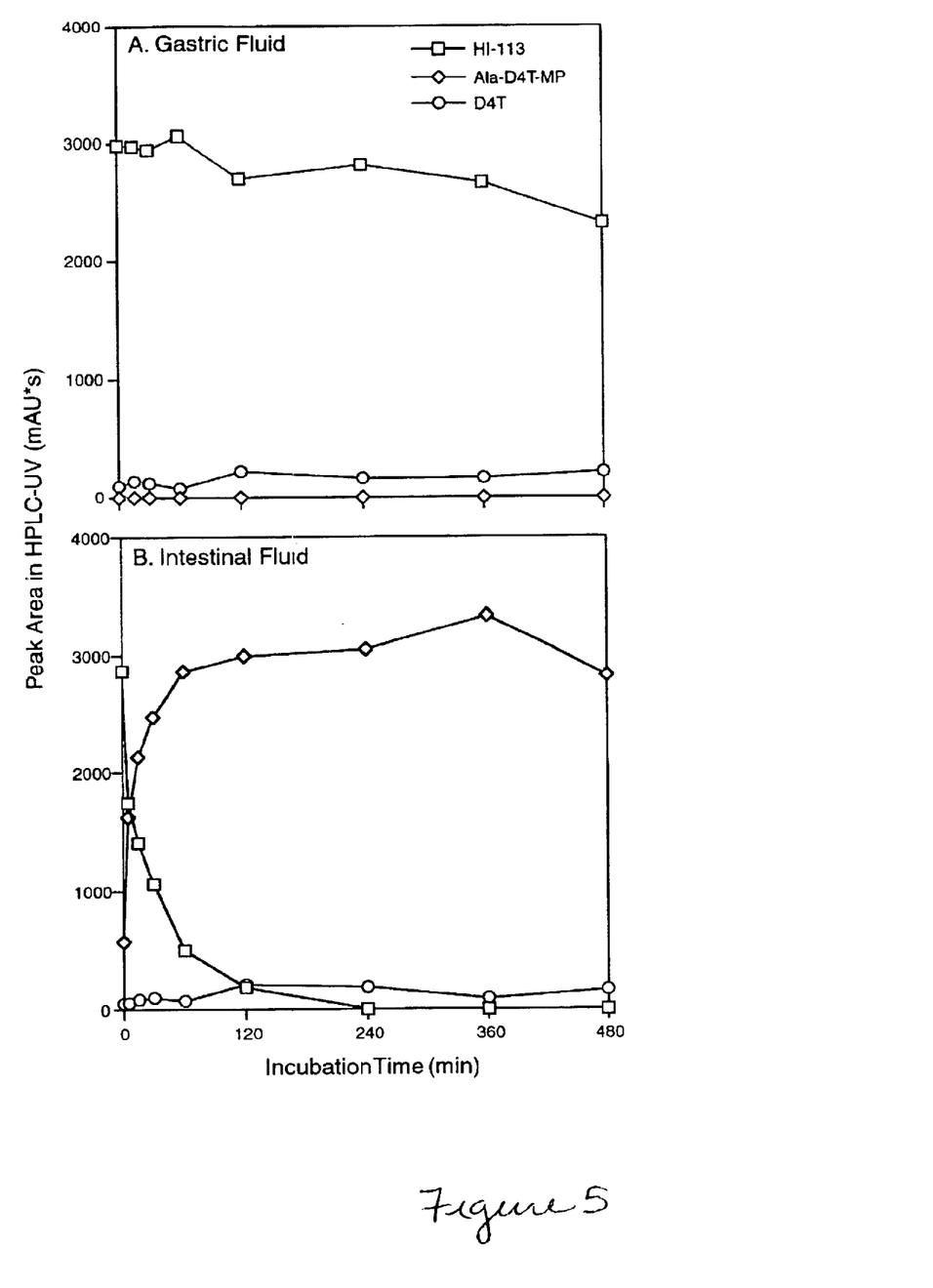
FIG. 5 is a plot showing the stability of HI-113 and formation of key metabolites in gastric fluid (A) and in intestinal fluid (B) as a function of time.

HI-113 is relatively stable in gastric fluid for 8 hours, but it is not stable in intestinal fluid (FIGS. 5A & 5B). HI-113 quickly decomposed to yield Ala-d4T-MP in intestinal fluid (approximately 94% of the HI-113 had decomposed within 2 hours). Ala-d4T-MP was stable in intestinal fluid; only a trace amount of d4T was detected in the intestinal fluid.

Example 6

Pharmacokinetic Studies in Mice

Female Balb/c mice (6–8 weeks old) from Taconic (Germantown, N.Y.) were housed in a controlled environment (12-hours of light/12-hours of dark, 22±1° C., 60±10% relative humidity), which is fully accredited by the USDA. All rodents were housed in microisolator cages (Lab Products, Inc., N.J.) containing autoclaved bedding. The mice were allowed free access to autoclaved pellet food and tap water throughout the study. All animal care procedures conformed to the Guide for the Care and Use of Laboratory Animals (National Research Council, National Academy Press, Washington D.C. 1996).

A solution (50 μl) of HI-113 (100 mg/kg) dissolved in DMSO was administered intravenously via the tail vein. This volume of DMSO is well-tolerated by mice when administrated by rapid intravenous or extravascular injection (Rosenkrantz et al., Cancer Chemother. Rep., 31, 7 (1963); Wilson et al., Toxicol. Appl. Pharmacol., 7, 104 (1965)). Blood samples (~500 μL) were obtained from the ocular venous plexus by retro-orbital venipuncture at 0, 2, 5, 10, 15, 30, 45, 60, 120, 240 and 360 minutes after intravenous injection. In order to study the pharmacokinetics of Ala-d4T-MP and d4T following systemic administration of these compounds, mice were injected with 75 mg/kg Ala-d4T-MP and 40 mg/kg d4T, respectively (these doses are equimolar to the 100 mg/kg HI-113).

In order to determine the pharmacokinetics of HI-113 following oral administration, 12 hour fasted mice were given a bolus dose of 100 mg/kg HI-113 via gavage using a #21 stainless-steel ball-tipped feeding needle. Sampling time points were 0, 2, 5, 10, 15, 30, 45, 60, 120, 240 and 360 minutes after the gavage.

All collected blood samples were heparinized and centrifuged at 7000×g for 5 minutes to separate the plasma fraction from the whole blood. The plasma samples were then processed immediately using the extraction procedure described above.

Figure 7:
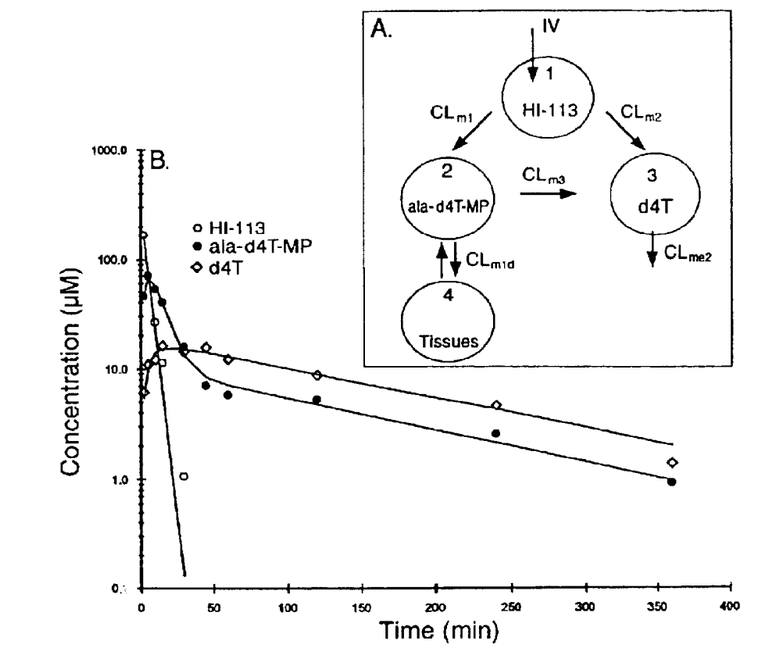
FIG. 7 shows (A) the pharmacokinetic model for describing HI-113, Ala-d4T-MP and d4T after intravenous injection of HI-113; and (B) the plasma concentrations of HI-113, Ala-d4T-MP and d4T as a function of time in Balb/C mice following intravenous injection of HI-113 (100 mg/kg, 4 mice per time-point).
Figure 8:
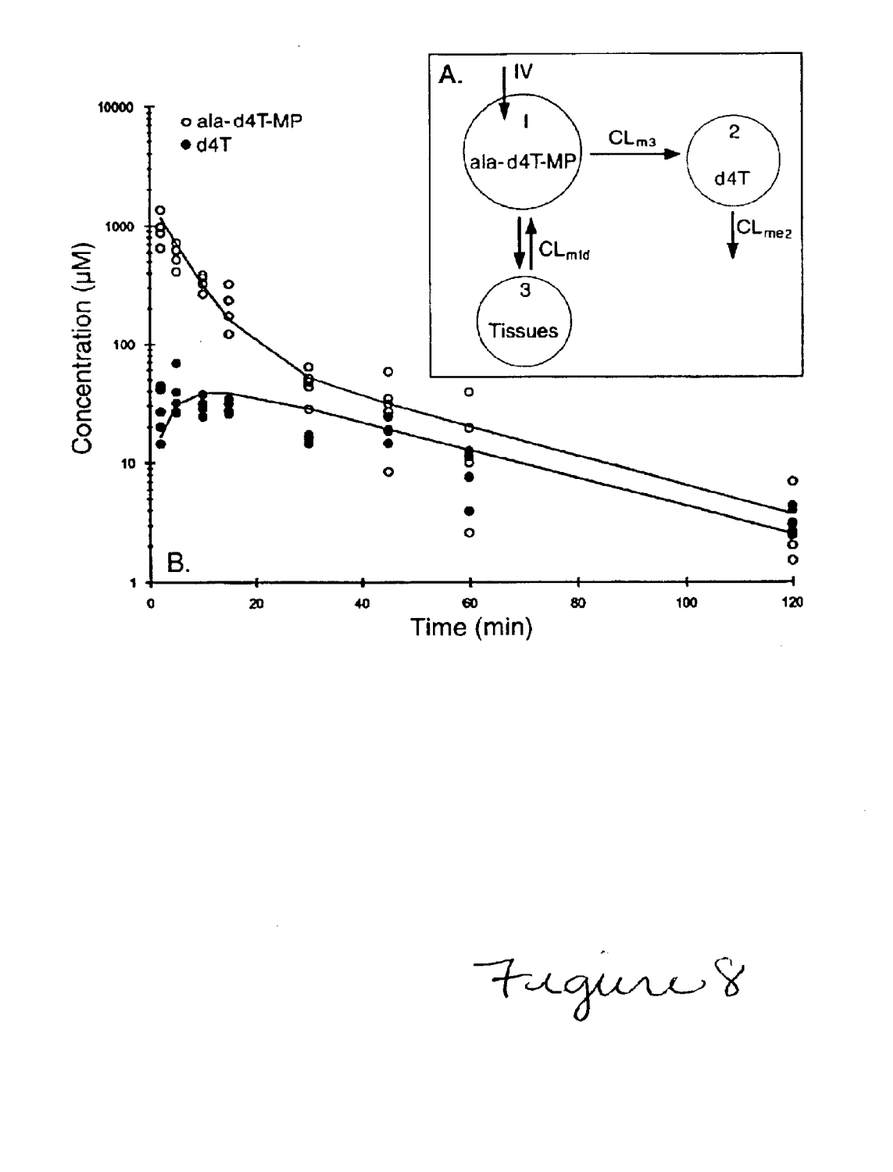
FIG. 8 shows (A) the pharmacokinetic model for describing Ala-d4T-MP and d4T after intravenous injection of Ala-d4T-MP; and (B) the plasma concentrations of Ala-d4T-MP and d4T as a function of time in Balb/C mice following intravenous injection of Ala-d4T-MP (75 mg/kg, 5 mice per time-point).

Pharmacokinetic modeling and parameter calculations were carried out using the WinNonlin Professional Version 3.0 (Pharsight, Inc., Mountain, Calif.) pharmacokinetics software (Chen et al., Pharm. Res., 16, 1003 (1999); Chen et al., Pharm. Res., 16, 117 (1999); Chen et al., J. Clin. Pharmacol., 39, 1248 (1999); Uckun et al., Clin. Cancer Res., 5, 2954 (1999); and Uckun et al., J. Pharmacol. Exp. Ther., 291, 1301 (1999)). An appropriate model was chosen on the basis of the lowest sum of weighted squared residuals, the lowest Schwartz Criterion (SC), the lowest Akaike's Information Criterion (AIC) value, the lowest standard errors of the fitted parameters, and the dispersion of the residuals. The elimination half-life was estimated by linear regression analysis of the terminal phase of the plasma concentration-time profile. The area under the concentration-time curve (AUC) was calculated according to the linear trapezoidal rule between the first sampling time (0 hours) and the last sampling time plus C/k, where C is the concentration of the last sampling and k is the elimination rate constant. The systemic clearance (CL) was determined by dividing the dose by the AUC. The metabolic clearance of the parent drug, the formation clearance of the metabolite, the clearance elimination of the metabolite, and the distribution clearance of the metabolite were estimated by simultaneous fitting of the concentration of parent drug and metabolites as a function of time curve to pharmacokinetic models (see FIGS. 7A & 8A) specified as a system of differential equations (Gabrielsson & Weiner, Phamacokinetic/Phamacodynamic Data Analysis: Concepts and Applications, Swedish Pharmaceutical Press (1997)). The fraction of HI-113 converted to a metabolite ($f_m$) was calculated as the ratio of the AUC for the metabolite after administration of the parent drug [$(AUC_m)_p$] to the AUC after administration of an equimolar dose of the metabolite [$(AUC_m)_m$] (Gibaldi & Perrier, 1982): $f_m=[(AUC_m)_p/D_p]\times[D_m/(AUC_m)_m]=(AUC_m)_p \cdot CL_m/D_p$ Example 7

Metabolism and Pharmacokinetic Profile of HI-113 Following Intravenous Administration Following intravenous administration, HI-113 (100 mg/kg) was metabolized to yield HI-113-M1 ($R_T$=15.3 minutes) and HI-113-M2 ($R_T$=18.5 minutes) (FIG. 1C). HI-113-M1 had the same retention time as Ala-d4T-MP, whereas HI-113-M2 had the same retention time as d4T (FIGS. 1B and 1C). The UV spectra of these two metabolites were identical to those of Ala-d4T-MP and d4T, respectively.

Figure 6:
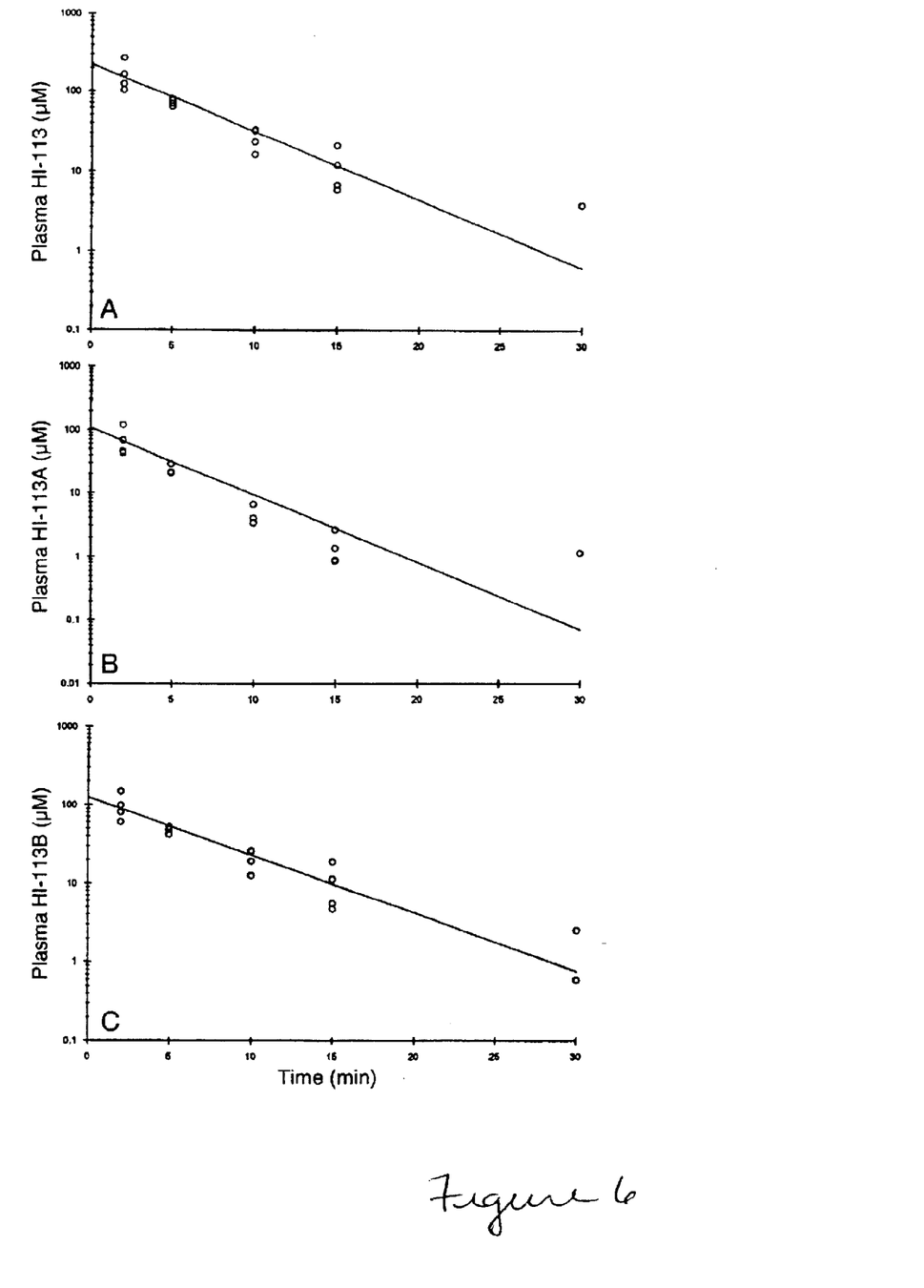
FIG. 6 shows plots of the plasma concentrations of total HI-113 (A), HI-113-A (B) and HI-113-B (C) as a function of time in Balb/C mice following intravenous injection of HI-113 (100 mg/kg, 4 mice per time-point).

After intravenous administration of 100 mg/kg HI-113, the plasma concentration of HI-113 as a function of time was described by a one-compartment model (FIG. 6A). The estimated pharmacokinetic parameter values are presented in Table 2. HI-113 had a $C_{max}$ of 224.2 μM and an AUC of 1142.0 μM·min. The systemic clearance of HI-113 was moderately fast with a CL of 160.9 mL/min/kg, which is approximately twice the rate of blood flow to the kidney or the liver (Davies et al., Pharm. Res., 10, 1093 (1993)). HI-13 had a moderate size volume of distribution with a $V_{SS}$ of 819.9 ml/kg, which is roughly equal to the total volume of water in the body. HI-113 had a short elimination half-life ($t_{1/2}$=3.5 minutes), however, because of its rapid metabolism.

The diastereomers of HI-113 were separated using the HPLC conditions described above (the retention times were 28.7 and 28.9 minutes). One of the diastereomers (HI-113-A, retention time=28.7 minutes) was metabolized more quickly than the other (HI-113-B, retention time=28.9 minutes; FIG. 1C). The pharmacokinetic features of these two diastereomers are summarized in Table 2. HI-113-B had a higher AUC (741.2 vs. 441.5 μM·min) and $C_{max}$ (125.7 vs. 107.9 μM) than HI-113-A (FIGS. 6B and 6C). HI-113-B also had a slightly longer elimination half-life than the HI-113-A diastereomer (4.1 minutes vs. 2.8 minutes), which can be due to the faster clearance of HI-13-A relative to that of HI-13-B (208.2 vs. 123.9 ml/min/kg). However, both of the HI-113 diastereomers were completely metabolized within 30 minutes.

Following intravenous injection, HI-113 was rapidly metabolized to yield Ala-d4T-MP ($t_{max}$=5.9 minutes; $C_{max}$=67.4 μM; $t_{1/2}$=129.2 minutes) and d4T ($t_{max}$=18.7 minutes; $C_{max}$=15.7 μM; $t_{1/2}$=114.8 minutes) as shown in Table 2.

TABLE 2

Estimated Pharmacokinetic Parameter Values for HI-113 and Its Metabolites in Balb/C Mice

| Measured | $V_{SS}$ (ml/kg) | AUC (μM · min) | $C_{max}$ (μM) | $t_{1/2}$ (min) | CL (ml/min/kg) | $t_{max}$ (min) |
|---|---|---|---|---|---|---|
| Total HI-113 | 819.9 | 1142.0 | 224.2 | 3.5 | 160.9 | ND |
|  | (920 ± 127.4) | (1071.8 ± 81.8) | (211.6 ± 29.3) | (3.6 ± 0.3) | (174.5 ± 13.2) |  |
| HI-113-A | 852.1 | 441.5 | 107.9 | 2.8 | 208.2 | ND |
|  | (1005.3 ± 134.0) | (359.7 ± 43.9) | (96.5 ± 12.8) | (2.6 ± 0.1) | (266.5 ± 30.2) |  |
| HI-113-B | 731.1 | 741.2 | 125.7 | 4.1 | 123.9 | ND |
|  | (791.8 ± 113.1) | (730.8 ± 45.7) | (123.1 ± 16.8) | (4.3 ± 0.4) | (127.3 ± 8.2) |  |

TABLE 2-continued

Estimated Pharmacokinetic Parameter Values for HI-113 and Its Metabolites in Balb/C Mice

| Measured | $V_{SS}$ (ml/kg) | AUC ($\mu$M · min) | $C_{max}$ ($\mu$M) | $t_{1/2}$ (min) | CL (ml/min/kg) | $t_{max}$ (min) |
|---|---|---|---|---|---|---|
| Ala-d4T-MP | ND | 2854.8 (2795.9 ± 361.2) | 67.4 (69.3 ± 4.1) | 129.2 (138.8 ± 40.2) | ND | 5.9 (5.1 ± 0.7) |
| d4T | ND | 2915.2 (2858.1 ± 182.2) | 15.7 (15.6 ± 1.2) | 114.8 (116.2 ± 11.9) | ND | 18.7 (17.4 ± 2.6) |

Pharmacokinetic parameters in Balb/c mice (N=4 mice per time-point) are presented as the average values estimated from composite plasma concentration-time curves of pooled data. The mean ±S.E.M values are indicated in parentheses. ND means the value was not determined.

The model depicted in FIGS. 7A and 7B describes the metabolite pharmacokinetics of Ala-d4T-MP and d4T after intravenous injection of HI-13. According to this model, HI-113 is biotransformed to produce Ala-d4T-MP ($CL_{m1}$) and d4T ($CL_{m2}$), respectively. Ala-d4T-MP derived from HI-113 can be further metabolized to form D4T ($CL_{m3}$) or distributed to the extravascular compartment ($Cl_{m1d}$). D4T produced from either HI-113 or Ala-d4T-MP is finally eliminated from the body ($CL_{me2}$). The pharmacokinetic parameters estimated for these two metabolites are presented in Table 3.

TABLE 3

Estimated Metabolite Pharmacokinetic Parameter Values

| Phamacokinetic Parameter | ml/min/kg |
|---|---|
| $CL_{m1}$ | 83.9 (21.5%) |
| $CL_{m2}$ | 87.4 (24.4%) |
| $CL_{m3}$ | 36.1 (85.9%) |
| $CL_{m1d}$ | 62.0 (69.8%) |
| $CL_{me2}$ | 47.1 (74.1%) |

The values in parenthesis are the C.V. of modeling. The metabolic clearance of HI-113 and the formation clearance of the metabolites were 83.9 ml/min/kg for Ala-d4T-MP and 87.4 ml/min/kg for d4T, respectively. The metabolic clearance of Ala-d4T-MP and the formation clearance of its metabolite, d4T, were 36.1 ml/min/kg, and a small portion of Ala-d4T-MP was distributed to the extravascular compartment with a $CL_{m1d}$ of 47.1 ml/min/kg. Finally, d4T was eliminated with a $CL_{me2}$ of 62.0 ml/min/kg.

Example 8

Pharmacokinetic Profile of Ala-d4T-MP Following Intravenous Administration

Following intravenous injection of Ala-d4T-MP (75 mg/kg, a dose equimolar to the 100 mg/kg dose of HI-113 discussed above), Ala-d4T-MP was quickly metabolized to yield d4T ($t_{max}$=4.4 minutes; $t_{1/2}$=34.0 minutes) (FIGS. 8A & 8B, Table 4). The concentration of Ala-d4T-MP as a function of time can be described using a two-compartment model, while a one-compartment model best fits the concentration of its metabolite, d4T, as a function of time (FIG. 8B). The $C_{max}$ values for Ala-d4T-MP and d4T were 1206.6 $\mu$M and 35.2 $\mu$M, respectively. The AUC was 11648.7 $\mu$M·min for Ala-d4T-MP and 1888.0 $\mu$M·min for d4T. The systemic clearance of Ala-d4T-MP was only 15.8 mL/min/kg (Table 4), which is much less than the blood flow to either the kidney or the liver (Davies et al., *Pharm. Res.*, 10, 1093 (1993)). Ala-d4T-MP also had a small volume of distribution ($V_{SS}$=275.5 ml/kg) that is less than the total volume of water in the body. Nevertheless, the elimination half-life of Ala-d4T-MP was short ($t_{1/2}$=28.5 minutes) due to its rapid metabolism.

TABLE 4

Estimated Pharmacokinetic Parameter Values for Ala-d4T-MP and Its Metabolite in Balb/C Mice

| Measured | $V_{SS}$ (ml/kg) | AUC ($\mu$M · min) | $C_{max}$ ($\mu$M) | $t_{1/2}$ (min) | CL (ml/min/kg) | $t_{max}$ (min) |
|---|---|---|---|---|---|---|
| Ala-d4T-MP | 275.5 (412.6 ± 126.3) | 11648.7 (11761.5 ± 447.2) | 1206.6 (1658.1 ± 544.9) | 28.5 (91.5 ± 54.5) | 15.8 (15.7 ± 0.6) | ND |
| d4T | ND | 1888.0 (1818.2 ± 42.9) | 35.2 (35.9 ± 3.7) | 34.0 (32.4 ± 2.2) | ND | 4.4 (5.0 ± 1.2) |

Pharmacokinetic parameters in Balb/c mice (N=5 mice per time-point) are presented as the average values estimated from composite plasma concentration-time curves of pooled data. The mean ±S.E.M values are indicated in parentheses. ND means the value was not determined.

The model depicted in FIG. 8A best described the metabolite pharmacokinetics after intravenous injection of Ala-d4T-MP. According to this model, Ala-d4T-MP can either be metabolized to form d4T ($CL_{m1}$) or distributed to the extravascular compartment ($Cl_{pd}$). D4T derived from Ala-d4T-MP is eliminated from the body ($CL_{me}$). By simultaneous fitting of the parent Ala-d4T-MP and d4T concentration values as a function of time to the described model, the metabolic clearance of Ala-d4T-MP and the formation clearance of d4T ($CL_{m1}$) were estimated to be 15.6 ml/min/kg as shown in Table 5.

TABLE 5

Estimated Metabolite Pharmacokinetic Parameter Values

| Pharmacokinetic Parameter | ml/min/kg |
| --- | --- |
| $CL_{m1}$ | 15.6 (16.6%) |
| $CL_{me}$ | 88.4 (13.0%) |
| $CL_{pd}$ | 4.7 (44.7%) |

The data in parentheses are the C.V. of modeling. A small portion of Ala-d4T-MP was distributed to extravascular compartment with a $CL_{pd}$ of 4.7 ml/min/kg and d4T derived from Ala-d4T-MP was finally eliminated with a relatively high $CL_{me}$ of 88.4 ml/min/kg. The $CL_{m1}$ of 15.6 ml/min/kg accounts for 99% of the total systemic clearance (CL=15.8 ml/min/kg) (see Table 4), indicating that most of Ala-d4T-MP is biotransformed to form d4T.

Example 9

Pharmacokinetic Profile of d4T Following Intravenous Administration

Figure 9:
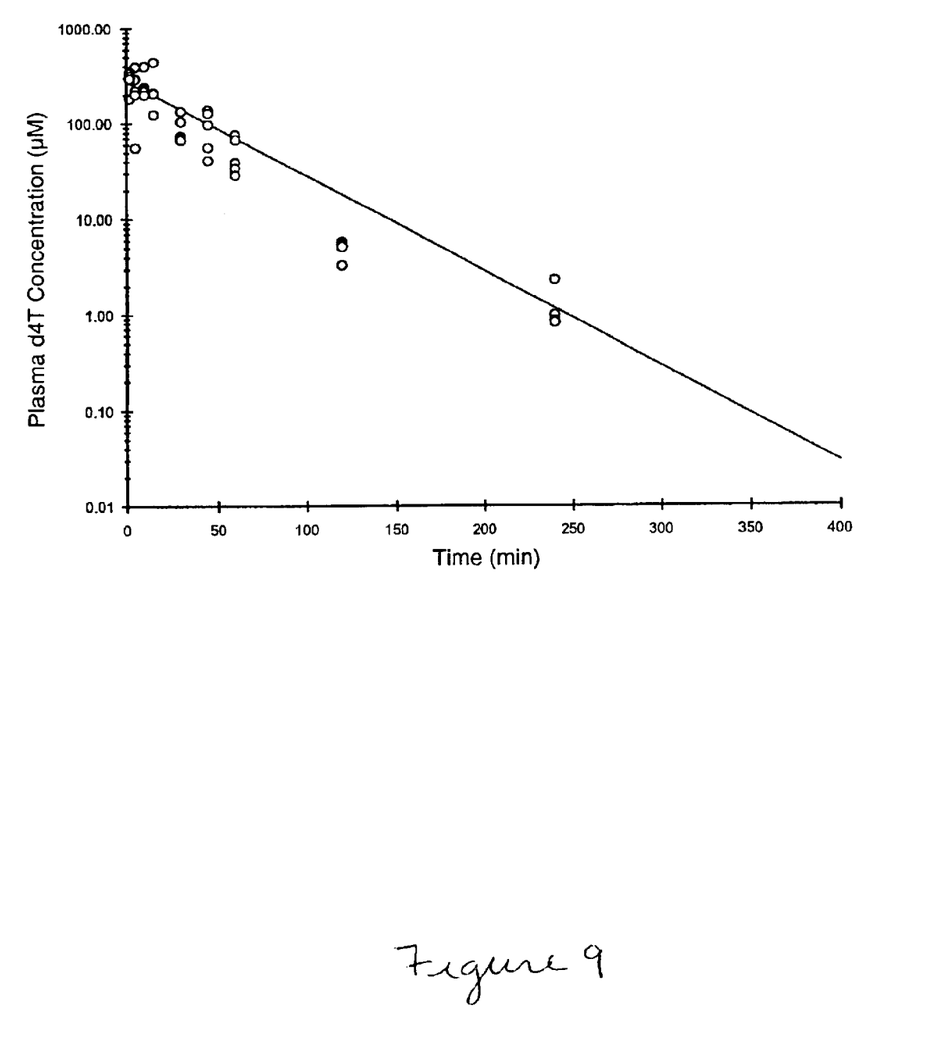
FIG. 9 shows the plasma concentration of d4T as a function of time in BALB/C mice following intravenous injection of D4T (40 mg/kg, 5 mice per time-point).

Following intravenous injection at a dose level of 40 mg/kg, a dose equimolar to the 100 mg/kg dose of HI-13, the concentration of d4T as a function of time was described using a one-compartment model (FIG. 9). The estimated pharmacokinetic parameter values are presented in Table 6. The estimated Cmax and AUC values for D4T were 279.5 $\mu$M and 12227.1 $\mu$M·min, respectively. D4T had a short elimination half-life (30.3 minutes). The systemic clearance of d4T was slow with a CL of only 15.0 ml/min/kg, which is much lower than the blood flow to either the kidney or the liver (Davies et al., *Pharm. Res.*, 10, 1093 (1993)). D4T had a moderately large volume of distribution ($V_{SS}$=657.8 ml/kg) that is approximately equal to the volume of water in the body.

TABLE 6

Estimated Pharmacokinetic Parameter Values for D4T in Balb/C Mice

| Measured | $V_{SS}$ (ml/kg) | AUC ($\mu$M · min) | $C_{max}$ ($\mu$M) | $t_{1/2}$ (min) | CL (ml/min/kg) |
| --- | --- | --- | --- | --- | --- |
| d4T | 657.8 | 12227.1 | 279.5 | 30.3 | 15.0 |
|  | (581.8 ± 62.8) | (12173.6 ± 559.5) | (318.9 ± 15.7) | (26.6 ± 1.2) | (15.2 ± 0.7) |

Pharmacokinetic parameters in Balb/c mice (N=5 mice per time-point) are presented as the average values estimated from composite plasma concentration-time curves of pooled data. The mean±S.E.M values are indicated in parentheses.

Example 10

Pharmacokinetic Profile of HI-113 following Oral Administration

Figure 10:
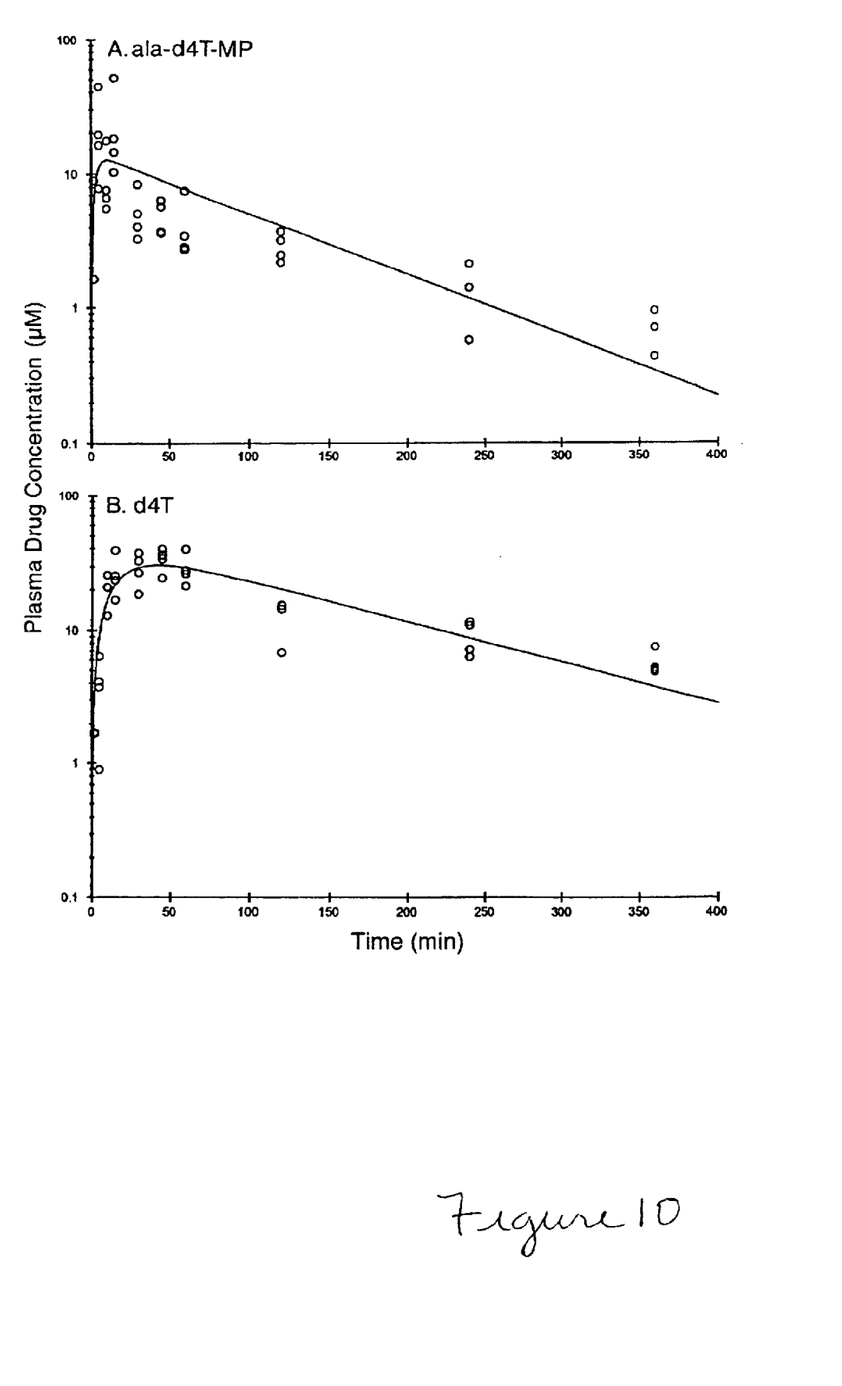
FIG. 10 shows the plasma concentrations of Ala-d4T-MP (A) and d4T (B) as a function of time in BALB/C mice following oral administration of HI-113 (100 mg/kg, 4 mice per time-point).

The pharmacokinetic behavior of orally administered HI-113 (100 mg/kg) was also examined. Both metabolites (Ala-d4T-MP and d4T) were detected, but the concentration of the parent HI-13 was below the detection limit (0.5 $\mu$M). The $t_{max}$ values are 10.3 minutes for Ala-d4T-MP and 42.4 minutes for d4T. A one-compartment pharmacokinetic model was used to describe both the Ala-d4T-MP and the d4T concentration changes as a function of time (FIGS. 10A and 10B). The estimated values for the pharmacokinetic parameters are presented in Table 7. The maximum concentrations ($C_{max}$) for Ala-d4T-MP and D4T are 12.7 $\mu$M and 30.7 $\mu$M, respectively. The elimination half-lives were 66.4 minutes and 99.0 minutes for Ala-d4T-MP and d4T, respectively.

TABLE 7

Estimated Pharmacokinetic Parameter Values Following Oral Administration of HI-113 in Balb/C Mice

| Measured | AUC ($\mu$M · min) | $C_{max}$ ($\mu$M) | $t_{1/2}$ (min) | $t_{max}$ (min) |
| --- | --- | --- | --- | --- |
| Ala-d4T-MP | 1350.5 | 12.7 | 66.4 | 10.3 |
|  | (1355.4 ± 88.2) | (15.6 ± 4.1) | (56.1 ± 8.5) | (9.3 ± 0.9) |
| d4T | 5905.3 | 30.7 | 99.0 | 42.4 |
|  | (5928.4 ± 294.6) | (29.5 ± 0.3) | (102.6 ± 3.8) | (45.2 ± 5.2) |

Pharmacokinetic parameters in Balb/c mice (N=4 mice per time-point) are presented as the average values estimated from composite plasma concentration-time curves of pooled data. The mean±S.E.M values are indicated in parentheses.

While a detailed description of the present invention has been provided above, the invention is not limited thereto. The invention described herein can be modified to include alternative embodiments, as will be apparent to those skilled in the art. All such alternatives should be considered within the spirit and scope of the invention, as claimed below.

We claim:

1. A method for extending the half-life of a compound of formula I in a mammal comprising administering to the mammal:

an esterase inhibitor, wherein the esterase inhibitor comprises paraoxon; and a compound of formula I;

wherein the compound of formula I is:

(I)

where $R_1$ is an aryl group substituted with an electron withdrawing group and $R_2$ is an amino acid residue or an ester of the amino acid residue, or a pharmaceutically acceptable salt thereof.

2. A method for extending the half-life of a compound of formula I in a mammal comprising administering to the mammal:
an esterase inhibitor, wherein the esterase inhibitor comprises physostigmine; and
a compound of formula I;
wherein the compound of formula I is:

(I)

where $R_1$ is an aryl group substituted with an electron withdrawing group and $R_2$ is an amino acid residue or an ester of the amino acid residue, or a pharmaceutically acceptable salt thereof.

3. A method for extending the half-life of a compound of formula I in a mammal comprising administering to the mammal:
an esterase inhibitor, wherein the inhibitor comprises a combination of paraoxon and physostigmine; and
a compound of formula I;
wherein the compound of formula I is:

(I)

where $R_1$ is an aryl group substituted with an electron withdrawing group and $R_2$ is an amino acid residue or an ester of the amino acid residue, or a pharmaceutically acceptable salt thereof.

4. The method of claim 1, wherein the aryl group is selected from the group consisting of phenyl, naphthyl, and anthryl.

5. The method of claim 1, wherein the aryl group is phenyl.

6. The method of claim 1, wherein the electron-withdrawing group is halo.

7. The method of claim 1, wherein $R_1$ is para-bromophenyl.

8. The method of claim 1, wherein $R_2$ is an α-amino acid or ester thereof.

9. The method of claim 1, wherein $R_2$ is —NHCH($CH_3$)COOCH$_3$.

10. The method of claim 1, wherein $R_1$ is para-bromophenyl and $R_2$ is —NHCH($CH_3$)COOCH$_3$.

11. The method of claim 1, wherein the compound of formula I is administered intravenously.

12. The method of claim 1, wherein the compound of formula I is administered orally.

13. The method of claim 1, wherein the compound of formula I and the esterase inhibitor are administered concurrently.

14. The method of claim 1, wherein the compound of formula I and the esterase inhibitor are administered in a single dosage form.

15. The method of claim 14, wherein the a single dosage form is a parenteral dosage form.

16. The method of claim 2, wherein the aryl group is selected from the group consisting of phenyl, naphthyl, and anthryl.

17. The method of claim 2, wherein the aryl group is phenyl.

18. The method of claim 2, wherein the electron-withdrawing group is halo.

19. The method of claim 2, wherein $R_1$ is para-bromophenyl.

20. The method of claim 2, wherein $R_2$ is an α-amino acid or ester thereof.

21. The method of claim 2, wherein $R_2$ is —NHCH($CH_3$)COOCH$_3$.

22. The method of claim 2, wherein $R_1$ is para-bromophenyl and $R_2$ is —NHCH($CH_3$)COOCH$_3$.

23. The method of claim 2, wherein the compound of formula I is administered intravenously.

24. The method of claim 2, wherein the compound of formula I is administered orally.

25. The method of claim 2, wherein the compound of formula I and the esterase inhibitor are administered concurrently.

26. The method of claim 2, wherein the compound of formula I and the esterase inhibitor are administered in a single dosage form.

27. The method of claim 2, wherein the a single dosage form is a parenteral dosage form.

28. The method of claim 3, wherein the and group is selected from the group consisting of phenyl, naphthyl, and anthryl.

29. The method of claim 3, wherein the aryl group is phenyl.

30. The method of claim 3, wherein the electron-withdrawing group is halo.

31. The method of claim 3, wherein $R_1$ is para-bromophenyl.

32. The method of claim 3, wherein $R_2$ is an α-amino acid or ester thereof.

33. The method of claim 3, wherein $R_2$ is —NHCH($CH_3$)COOCH$_3$.

34. The method of claim 3, wherein $R_1$ is para-bromophenyl and $R_3$ is —NHCH($CH_3$)COOCH$_3$.

35. The method of claim 3, wherein the compound of formula I is administered intravenously.

36. The method of claim 3, wherein the compound of formula I is administered orally.

37. The method of claim 3, wherein the compound of formula I and the esterase inhibitor are administered concurrently.

38. The method of claim 3, wherein the compound of formula I and the esterase inhibitor are administered in a single dosage form.

39. The method of claim 3, wherein the a single dosage form is a parenteral dosage form.

* * * * *